(12) United States Patent
Jackson et al.

(10) Patent No.: US 7,501,544 B2
(45) Date of Patent: Mar. 10, 2009

(54) PROCESS FOR THE PRODUCTION OF CYCLIC DIKETONES

(75) Inventors: David Anthony Jackson, Muenchwilen (CH); Andrew Edmunds, Basel (CH); Martin Charles Bowden, Huddersfield (GB); Ben Brockbank, Huddersfield (GB)

(73) Assignees: Syngenta Crop Protection, Inc., Greensboro, NC (US); Syngenta Limited (GB)

( * ) Notice: Subject to any disclaimer, the term of this patent is extended or adjusted under 35 U.S.C. 154(b) by 0 days.

(21) Appl. No.: 11/568,337

(22) PCT Filed: Apr. 29, 2005

(86) PCT No.: PCT/EP2005/004681

§ 371 (c)(1),
(2), (4) Date: Oct. 26, 2006

(87) PCT Pub. No.: WO2005/105745

PCT Pub. Date: Nov. 10, 2005

(65) Prior Publication Data

US 2007/0232837 A1 Oct. 4, 2007

(30) Foreign Application Priority Data

Apr. 30, 2004 (CH) .................................. 00765/04

(51) Int. Cl.
*C07C 49/76* (2006.01)
*C07C 45/00* (2006.01)
(52) U.S. Cl. ........................................ 568/308; 568/323
(58) Field of Classification Search ................. 568/303, 568/323
See application file for complete search history.

(56) References Cited

U.S. PATENT DOCUMENTS 6,316,390 B1 * 11/2001 Nakamura et al. .......... 504/288

OTHER PUBLICATIONS

Mewshaw, Richard E.: "Vilsmeier reagents: preparation of .beta.-halo-.alpha.,.beta.-unsaturated ketones;" Tetrahedron Letters, 30(29), 3753-6, Coden: TELEAY; ISSN: 0040-4039, 1989, XP000034043, p. 3755; table 1 3rd column, 1st, 3rd, 4th compounds.
Fu X et al: "A copper-free palladium catalyzed cross coupling reaction of vinyl tosylates with terminal acetylenes", Tetrahedron Letters, Elsevier Science Publishers, Amsterdam, NL, vol. 43, No. 37, Sep. 9, 2002, pp. 6673-6676, XP004376229; ISSN: 0040-4039; p. 6673, compound 2.
Ioannis N. Houpis: "Palladium (II)-catalyzed coupling of 2-carboxyethyl enol triflates with organostannanes", Tetrahedron Letters, vol. 32, No. 46, 1991, pp. 6675-6678, XP002342412, p. 6676; table 1; compound 5.

Tong, Zhiwei et al: "Synthesis and oxidation reactions of cycloheptatrienyl sulfones", Tetrahedron Letters, 41(41), 7795-7799 Coden: TELEAY; ISSN: 0040-4039, 2000, XP004235873, p. 7798; compound 29.
Stern, Alan J. et al: Oxygenophilic organoaluminum-mediated conjugate addition of alkyllithium and Gringnard reagents to guinone monoketals and quinol ethers. The directing effect of methoxy group on the 1,4-addition process, Journal of Organic Chemistry, 54(18), 4413-19 Coden: JOCEAH; ISSN: 0022-3263, 1989, XP002342407, p. 4414; table I; compound 9.

(Continued)

*Primary Examiner*—Sikarl A Witherspoon
(74) *Attorney, Agent, or Firm*—William A. Teoli, Jr.

(57) ABSTRACT

The present invention relates to a process for the preparation of compounds of formula (I), wherein the substituents are as defined in claim 1, by reacting a compound of formula (II), either with a chlorination or bromination agent or with a compound of formula (III) Cl—$SO_2R_9$, $R_9$ being $C_1$-$C_4$alkyl, $C_1$-$C_4$haloalkyl, phenyl or $C_1$-$C_4$alkyl-substituted phenyl, to form the compound of formula (IV), reacting the compound of formula (IV) with a compound of formula (V) $M^+$-$O^-$—C(O)—Y wherein Y is as defined above and $M^+$ is the hydrogen cation or an alkali metal ion, alkaline earth metal ion or ammonium ion, to form the compound of formula (VI) and treating that compound with a cyanide source in the presence of a base.

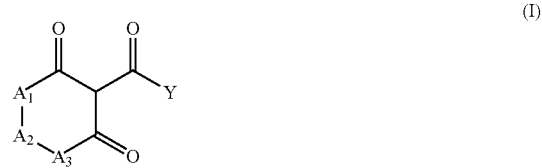

(I)

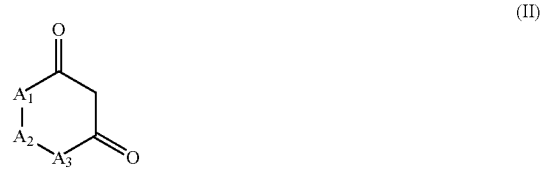

(II)

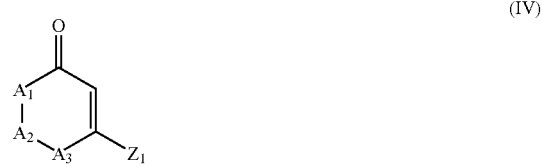

(IV)

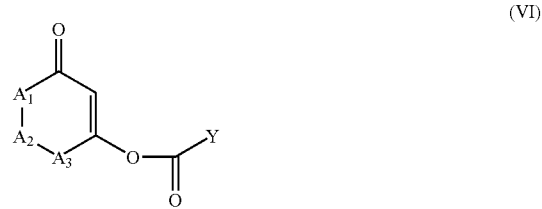

(VI)

3 Claims, No Drawings

OTHER PUBLICATIONS

Subramaniam, L. R. et al: "Hydrogenative cleavage of phenolic and enolic perfluroalkanesulfonates;" Synthesis, (6), 481-5 Coden: SYNTBF; ISSN: 0039-7881, 1984, XP002342408, p. 482; table 1; compound F.

Database CA 'Online! Chemical Abstracts Service, Columbus, Ohio, US; 1988, Stern, Alan J. et al: Oxygenophilic organoaluminum-promoted 1,4-addition of organolithium reagents to quinone monoacetals; XP002342423, retrieved from STN Database accession No. 1989: 172723 abstract, RN=119927-94-5 & Journal of The Chemical Society Chemical Communications, (18), 1255-6 Coden: JCCAT; ISSN: 0022-4936, 1988.

Database CA 'Online! Chemical Abstracts Service, Columbus, Ohio, US; 1981; Garcia Martinez, A. et al: "Reaction of some triflates with n-butyllithium"; XP002342424, retrieved from STN, Database accession No. 1982:438548, abstract, RN=82095-45-2; RN=82095-46-3, & Anales De Quimica Serie C: Quimica Organica Y Biquimica, 77(2), 150-2 Coden: AQSBD6; ISSN: 0211-1357, 1981.

Database CA Online! Chemical Abstracts Service, Columbus, Ohio, US; 1978, Buchi, George et al: "The total synthesis of mollicellin A"; XP002342425; retrieved from STN, Database accession No. 1979:204059 abstract, RN=70265-66-6; & Heterocycles, 11, 437-42 Coden: HTCYAM; ISSN: 0385-5414, 1978.

Database CA Online! Chemical Abstracts Service, Columbus, Ohio, US; 1975, Nishizawa, Kyoko et al: "Covenient synthesis of substituted pyrocatechols"; XP002342426; retrieved from STN, Database Accession No. 1975:496634, abstract, RN=57341-93-2 & Bulletin of the Chemical Society of Japan, 48(7), 2215-16 Coden: BCSJA8; ISSN: 0009-2673, 1975.

Tamura, Yasumitsu et al.: "Nonsteroidal antiinflammatory agents. 1. 5-Alkoxy-3-biphenyl7ylacetic acids and related compounds as new potential antiinflammatory agents"; Journal of Medicinal Chemistry, 20(5), 709-14 Coden: JMCMAR; ISSN: 0022-2623, 1977, XP002025861, p. 709, right-hand column, compounds 2, 3.

Ian Fleming; "A synthesis of (-)-(R)-trans-beta-(1,2,3-trimethylcyclope nt-2-enyl)acrylic acid"; Journal of the Chemical Society, Perkins Transations 1: Organic and Bio-Organic Chemistry;, vol. 16, 1973, pp. 1653-1657, XP009052925, p. 1653, left hand column, compounds 5,6.

Clark, Robin D. et al: "Preparation and reactions of .beta-chloro-.alpha.,.beta.-unsaturated ketones"; Journal of Organic Chemistry, 41(4),636-43 Coden: JOCEAH; ISSN: 0022-3263, 1976, XP002342410, p. 636, right-hand column; compounds 6,7 p. 640; table III, compounds 7, 10, 12.

Conrad J. Kowalski & Co.: "Enone mesylates, Precursors to beta-substituted cyclohexenoes", J. Org. Chem, vol. 46, 1981, pp. 197-201,XP002342411, Indiana, USA, p. 198; table I; compounds 1,2; p. 199; table I; compounds 2A, 2B, 7A, 7B, 8A, 8B.

Qing T et al: "Carbomethoxypropionyl Cyanide: A regioselective C-Acylation Reagent for the Preparation of beta-Dicarbonyl Compounds"; Tetrahedron Letters, Elsevier Science Publishers, Amsterdam, NL, vol. 39, No. 16, Apr. 16, 1998, pp. 2249-2252, XP004111142, ISSN: 0040-4039, p. 2251; compound 7.

Toshio Isobe: "2-chloro-1,3-dimethylimidazolinium chloride. A powerful dehydrating equivalent to DCC"; J. Ort. Chem., vol. 64, 1999, pp. 6984-6988, XP002342413, p. 6986, right-hand column, scheme 2.

Ariamala Gopalsamy: "Parallel solid-phase synthesis of vitronectin receptor inhibitors", Bioorganic & Medicinal Chemistry Letters, vol. 10, 2000, pp. 1715-1718, XP002342414, p. 1718, right-hand column reaction scheme.

F. A. Lakhvich: "Synthesis of 2-(5-methoxycarbonylpentanonyl)-5,6-dimethy 1-2-cyclohexen-1-one and its reaction with some CH acids"; Russian Journal of Organic Chemistry, vol. 29, 1993, pp. 518,523, XP009052855, p. 518, last paragraph, p. 519, paragraph 1-4.

K. Fries: "neus uber dichlor-2,3-naphtochinon-1,4" Chem. Ber., vol. 56, 1923, pp. 1291-1303, XP002078404, the whole document.

\* cited by examiner

PROCESS FOR THE PRODUCTION OF CYCLIC DIKETONES

This application is a 371 of International Application No. PCT/EP2005/004681 filed Apr. 29, 2005, which claims priority to CH 00765/04 filed April 30, 2004, the contents of which are incorporated herein by reference.

The present invention relates to a process for the preparation of cyclic 1,3-diketone derivatives carbonylated in the 2-position.

Processes for the preparation of cyclic 1,3-diketones substituted in the 2-position by an arylcarbonyl group are described, for example, in WO/0015615, WO 00/37437, WO 01/66522 and WO 01/94339. The compounds disclosed therein have herbicidal action.

According to WO 01/94339, such cyclic 1,3-diketones can be prepared by
a) reacting a compound of formula A

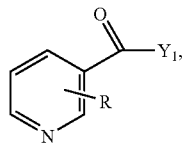
(A)

wherein $Y_1$ is a leaving group such as, for example, halogen or cyano and R is an organic substituent, in an inert, organic solvent, in the presence of a base, with a cyclohexanedione of formula B

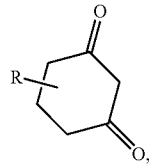
(B)

wherein R is an organic substituent, to form compounds of formula C

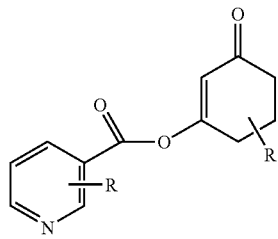
(C)

and then isomerising those compounds, for example in the presence of a base and a catalytic amount of dimethylaminopyridine or a cyanide source.

However, such processes have the disadvantage that, in order to prepare the starting compounds of formula A from the acid on which they are based, an additional activation step is required for introduction of the leaving group. A further problem in the preparation of the compound of formula A is the instability of the starting compounds and the instability of the compound of formula A itself, which frequently makes the reaction procedure difficult. This is a serious disadvantage especially for large-scale production.

The problem of the present invention is accordingly to make available a novel general process for the preparation of monocyclic and bicyclic 1,3-diketones which makes it possible to prepare such compounds in high yields and good quality with a simple reaction procedure and little outlay without the above-mentioned disadvantages of the known processes.

The present invention accordingly relates to a process for the preparation of compounds of formula I

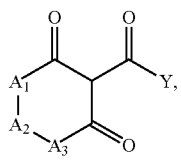
(I)

wherein Y is an organic substituent which is so selected that the compound of formula I has a pK value of from 1 to 5;

$A_1$ is $CR_1R_2$;

$A_2$ is oxygen, $C(O)$, $SO_2$ or $(CR_3R_4)_n$;

n is 1 or 2;

$A_3$ is $CR_5R_6$;

$R_1, R_2, R_3, R_4, R_5$ and $R_6$ are each independently of the others $C_1$-$C_4$alkyl which may mono-, di- or tri-substituted by $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or by heteroaryl, it being possible for the phenyl and heteroaryl groups in turn to be mono-, di- or tri-substituted by $C_1$-$C_4$alkoxy, halogen, hydroxy, cyano, hydroxycarbonyl, $C_1$-$C_4$alkoxycarbonyl, $C_1$-$C_4$alkylsulfonyl or by $C_1$-$C_4$haloalkyl, the substituents on the nitrogen in the heterocyclic ring being other than halogen; and/or $R_1, R_2, R_3, R_4, R_5$ and $R_6$ are each independently of the others hydrogen, $C_1$-$C_4$alkoxy, halogen, hydroxy, cyano, hydroxycarbonyl, $C_1$-$C_4$alkoxycarbonyl, $C_1$-$C_4$alkylthio, $C_1$-$C_4$alkylsulfinyl, $C_1$-$C_4$alkylsulfonyl, $C_1$-$C_4$alkylcarbonyl, phenyl or heteroaryl, it being possible for the phenyl and heteroaryl groups in turn to be mono-, di- or tri-substituted by $C_1$-$C_4$alkoxy, halogen, hydroxy, cyano, hydroxycarbonyl, $C_1$-$C_4$alkoxycarbonyl, $C_1$-$C_4$alkylsulfonyl or by $C_1$-$C_4$haloalkyl, the substituents on the nitrogen in the heterocyclic ring being other than halogen; and/or $R_1$ and $R_2$ together form a 3- to 5-membered carbocyclic ring which may be substituted by $C_1$-$C_4$alkyl and/or interrupted by oxygen, sulfur, $S(O)$, $SO_2$, $OC(O)$, $NR_7$ or by $C(O)$; and/or $R_2$ and $R_4$ together or $R_2$ and $R_5$ together form a $C_1$-$C_3$alkylene chain which may be interrupted by oxygen, sulfur, SO, $SO_2$, $OC(O)$, $NR_8$ or by $C(O)$; it being possible for that $C_1$-$C_3$alkylene chain in turn to be substituted by $C_1$-$C_4$alkyl; and $R_7$ and $R_8$ are each independently of the other $C_1$-$C_4$alkyl, $C_1$-$C_4$haloalkyl, $C_1$-$C_4$alkyl $C_1$-$C_4$alkylcarbonyl or $C_1$-$C_4$alkoxycarbonyl; in which process a) a compound of formula II

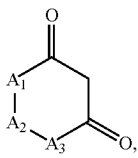

(II)

wherein $A_1$, $A_2$ and $A_3$ are as defined for formula I, is reacted, in the presence of a water-immiscible solvent, in the presence of a base or a catalytic amount of a tertiary amide, either with a chlorination or bromination agent or with a compound of formula III

$Cl-SO_2R_9$ (III), wherein $R_9$ is $C_1$-$C_4$alkyl, $C_1$-$C_4$haloalkyl, phenyl or $C_1$-$C_4$alkyl-substituted phenyl, to form the compound of formula IV

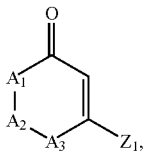

(IV)

wherein $A_1$, $A_2$ and $A_3$ are as defined for formula I and $Z_1$ is chlorine, bromine or $OSO_2R_9$, $R_9$ being as defined hereinbefore;

b) the compound of formula IV is converted, using a compound of formula V

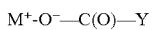

$M^+$-$O^-$—$C(O)$—Y (V), wherein Y is as defined hereinbefore and $M^+$ is the hydrogen cation or an alkali metal ion, alkaline earth metal ion or ammonium ion, preferably hydrogen, the sodium ion or ammonium ion, into the compound of formula VI

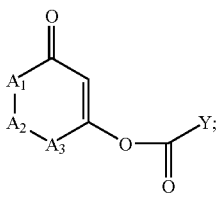

(VI)

and c) then the compound of formula VI is treated with a cyanide source in the presence of a base.

The organic substituent Y may be a substituent of any desired structure provided that it remains substantially inert under the reaction conditions of the process according to the invention.

Y is preferably a mono-, di- or tri-substituted phenyl, pyridyl or heteroaryl group, especially a di- or tri-substituted phenyl group or a di-substituted 2-pyridyl or 3-pyridyl group, the substitution pattern of those groups being freely selectable provided that the groups remain substantially inert under the reaction conditions of the process according to the invention. Preference is given to phenyl, 3-pyridyl and heteroaryl groups which carry at least one substituent located, very especially, in the ortho position.

Especially advantageously, it is possible, using the process according to the invention, to prepare compounds of formula I wherein Y is

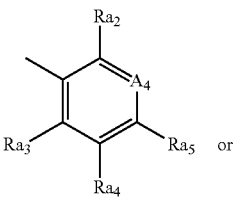

($Q_1$)

or

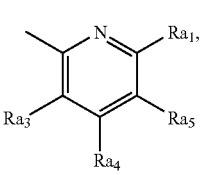

($Q_2$)

wherein
$A_4$ is $CRa_1$ or $=N-(O)_p$;
p is 0 or 1;
$Ra_1$ is hydrogen, $C_1$-$C_6$alkyl, hydroxy, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_1$-$C_4$alkylcarbonyloxy, $C_1$-$C_4$alkylsulfonyloxy, phenylsulfonyloxy, $C_1$-$C_6$alkylthio, $C_1$-$C_6$alkylsulfinyl, $C_1$-$C_6$alkylsulfonyl, $C_1$-$C_6$alkylamino, di($C_1$-$C_6$alkyl)amino, $C_1$-$C_3$alkoxy-$C_1$-$C_3$alkylamino, $C_1$-$C_3$alkoxy-$C_1$-$C_3$alkyl-N($C_1$-$C_3$alkyl)-, $C_1$-$C_4$alkoxycarbonyl, $C_1$-$C_6$haloalkyl, formyl, cyano, halogen, phenyl or phenoxy, it being possible for the phenyl-containing groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro;

or $Ra_1$ is a three- to ten-membered monocyclic or together with $Ra_2$ or $Ra_5$ annellated bicyclic ring system which may be interrupted once or up to three times by heterocyclic substituents selected from oxygen, sulfur, S(O), $SO_2$, N($Ra_6$), carbonyl and C($=NORa_7$), the ring system, unless it is annellated, being bonded to the carbon atom of the substituent $A_4$ either directly or by way of a $C_1$-$C_4$alkylene, $C_1$-$C_4$alkenylene or $C_2$-$C_4$alkynylene bridge which may be interrupted by oxygen, $-N(C_1$-$C_4$alkyl)-, sulfur, sulfinyl or by sulfonyl, and the ring system may contain not more than 2 oxygen atoms and not more than two sulfur atoms, and the ring system may in turn be mono-, di- or tri-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_3$-$C_6$alkenyloxy, $C_3$-$C_6$alkynyloxy, $C_1$-$C_6$alkylthio, $C_1$-$C_6$haloalkylthio, $C_3$-$C_6$akenylthio, $C_3$-$C_6$haloalkenylthio, $C_3$-$C_6$alkynylthio, $C_1$-$C_4$alkoxy-$C_1$-$C_2$alkylthio, $C_1$-$C_4$-$C_2$alkylthio, $C_1$-$C_4$alkoxycarbonyl-$C_1$-$C_2$alkylthio, cyano-$C_1$-$C_4$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_4$alkylaminosulfonyl, di($C_1$-$C_4$alkyl)aminosulfonyl, di($C_1$-$C_4$alkyl)amino, halogen, cyano, nitro, phenyl, benzyloxy and/or by benzylthio, and it being possible for the phenyl-containing groups in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and substituents on the nitrogen in the heterocyclic ring are other than halogen;

or $Ra_1$ is the group -$X_5$-$X_7$ or the group -$X_6$-$X_5$-$X_7$; wherein
$X_5$ is oxygen, —O(CO)—, —(CO)O—, —O(CO)O—, —N($C_1$-$C_4$alkyl)—O—, —O—N($C_1$-$C_4$alkyl)-, sulfur, sulfinyl, sulfonyl, —$SO_2$N($C_1$-$C_4$alkyl)-, —N($C_1$-$C_4$alkyl)$SO_2$—, —N($C_1$-$C_2$alkoxy-$C_1$-$C_2$alkyl)$SO_2$— or —N($C_1$-$C_4$alkyl)-;

$X_6$ is a $C_1$-$C_6$alkylene, $C_3$-$C_6$alkenylene or $C_3$-$C_6$alkynylene chain which may be mono- or poly-substituted by halogen or by $X_8$, the unsaturated bonds of the chain not being bonded directly to the substituent $X_5$;

$Ra_6$ is hydrogen, $C_1$-$C_4$alkyl, $C_1$-$C_4$alkylthio-$C_1$-$C_4$alkylcarbonyl, $C_1$-$C_4$alkylsulfinyl-$C_1$-$C_4$alkylcarbonyl, $C_1$-$C_4$alkylsulfonyl-$C_1$-$C_4$alkylcarbonyl, $C_1$-$C_4$alkoxycarbonyl, $C_1$-$C_4$alkylcarbonyl, phenylcarbonyl or phenyl, it being possible for the phenyl groups in turn to be substituted by $C_1$-$C_4$alkyl, $C_1$-$C_4$haloalkyl, $C_1$-$C_4$alkoxy, $C_1$-$C_4$haloalkoxy, $C_1$-$C_4$alkylcarbonyl, $C_1$-$C_4$alkylamino, di($C_1$-$C_4$alkyl)amino, $C_1$-$C_4$alkylthio, $C_1$-$C_4$alkylsulfinyl, $C_1$-$C_4$alkyl-$SO_2$, $C_1$-$C_4$alkyl-S(O)$_2$O, $C_1$-$C_4$haloalkylthio, $C_1$-$C_4$haloalkylsulfinyl, $C_1$-$C_4$haloalkyl-$SO_2$, $C_1$-$C_4$haloalkyl-S(O)$_2$O, $C_1$-$C_4$alkyl-S(O)$_2$NH, $C_1$-$C_4$alkyl-S(O)$_2$N($C_1$-$C_4$alkyl)-, halogen, nitro or by cyano;

$Ra_7$ is hydrogen, $C_1$-$C_4$alkyl, $C_3$-$C_4$alkenyl, $C_3$-$C_4$alkynyl or benzyl;

$Ra_2$ is hydrogen, $C_1$-$C_6$alkyl, $C_1$-$C_6$haloalkyl, $C_2$-$C_6$alkenyl, $C_2$-$C_6$haloalkenyl; vinyl substituted by $C_1$-$C_2$alkoxycarbonyl or by phenyl; or $C_2$-$C_6$alkynyl, $C_2$-$C_6$haloalkynyl; or ethynyl substituted by trimethylsilyl, hydroxy, $C_1$-$C_6$alkoxy, $C_1$-$C_4$alkoxycarbonyl or by phenyl;

$C_3$-$C_6$allenyl, $C_3$-$C_6$cycloalkyl or halo- or $C_1$-$C_3$alkoxymethyl-substituted $C_3$-$C_6$cycloalkyl; or $C_1$-$C_6$alkoxy, $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_4$alkoxy, $C_1$-$C_4$alkoxy-$C_1$-$C_4$alkoxy, $C_1$-$C_4$alkylthio-$C_1$-$C_4$alkoxy, $C_1$-$C_4$alkylsulfinyl-$C_1$-$C_4$alkoxy, $C_1$-$C_4$alkylsulfonyl-$C_1$-$C_4$alkoxy, $C_1$-$C_4$alkoxycarbonyl-$C_1$-$C_4$alkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_4$alkoxycarbonyl-$C_1$-$C_4$alkylthio, $C_1$-$C_4$alkoxycarbonyl-$C_1$-$C_4$alkylsulfinyl, $C_1$-$C_4$alkoxycarbonyl-$C_1$-$C_4$alkylsulfonyl, $C_1$-$C_6$alkylamino, di($C_1$-$C_6$-alkylsulfinyl, $C_1$-$C_3$alkoxy-$C_1$-$C_3$alkylamino, $C_1$-$C_3$alkoxy-$C_1$-$C_3$alkyl-N($C_1$-$C_3$alkyl), $C_1$-$C_6$-alkylaminosulfonyl, di($C_1$-$C_6$alkyl)aminosulfonyl, $C_1$-$C_4$alkylsulfonyloxy, $C_1$-$C_4$haloalkylsulfonyloxy, $C_1$-$C_4$alkylsulfonylamino, $C_1$-$C_4$alkylsulfonyl-N($C_1$-$C_4$alkyl), cyano, carbamoyl, $C_1$-$C_4$alkoxycarbonyl, formyl, halogen, rhodano, amino, hydroxy-$C_1$-$C_4$alkyl, $C_1$-$C_4$alkoxy-$C_1$-$C_4$alkyl, $C_1$-$C_4$alkylthio-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl, cyano-$C_1$-$C_4$alkyl, $C_1$-$C_6$alkylcarbonyloxy-$C_1$-$C_4$alkyl, $C_1$-$C_4$alkoxycarbonyl-$C_1$-$C_4$-alkyl, $C_1$-$C_4$alkoxycarbonyloxy-$C_1$-$C_4$alkyl, rhodano-$C_1$-$C_4$alkyl, phenyl-$C_1$-$C_4$alkyl, phenoxy-$C_1$-$C_4$alkyl, benzyloxy-$C_1$-$C_4$alkyl, benzoyloxy-$C_1$-$C_4$alkyl, (2-oxiranyl)-$C_1$-$C_4$alkyl, $C_1$-$C_4$alkylamino-$C_1$-$C_4$alkyl, di($C_1$-$C_4$alkyl)amino-$C_1$-$C_4$alkyl, $C_1$-$C_{12}$alkylthiocarbonyl-$C_1$-$C_4$alkyl or formyl-$C_1$-$C_4$alkyl, benzylthio, benzylsulfinyl, benzylsulfonyl, benzyloxy, benzyl, phenyl, phenoxy, phenylthio, phenylsulfinyl or phenylsulfonyl; it being possible for the phenyl-containing groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro; or $Ra_2$ is a three- to ten-membered monocyclic or annellated bicyclic ring system which may be aromatic, saturated or partially saturated and may contain from 1 to 4 hetero atoms selected from nitrogen, oxygen and sulfur, the ring system being bonded to the group $Q_1$ or $Q_2$ directly or by way of a $C_1$-$C_4$alkylene, $C_1$-$C_4$alkenylene or $C_2$-$C_4$alkynylene bridge which may be interrupted by oxygen, —N($C_1$-$C_4$alkyl)-, sulfur, sulfinyl, sulfonyl or by carbonyl; and each ring system may contain not more than 2 oxygen atoms and not more than two sulfur atoms, and the ring system may in turn be mono-, di- or tri-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkylthio, $C_3$-$C_6$alkenyloxy, $C_3$-$C_6$alkynyloxy, hydroxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_4$alkoxy-$C_1$-$C_3$alkylthio, $C_1$-$C_4$alkylcarbonyl-$C_1$-$C_3$alkylthio, $C_1$-$C_4$alkoxycarbonyl-$C_1$-$C_3$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_4$alkylaminosulfonyl, di($C_1$-$C_4$alkyl)aminosulfonyl, di($C_1$-$C_4$alkyl)amino, halogen, cyano, nitro, phenyl and/or by benzylthio; it being possible for phenyl and benzylthio in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and substituents on the nitrogen in the heterocyclic ring are other than halogen; or $Ra_2$ is the group -$X_1$-$X_3$ or the group -$X_2$-$X_1$-$X_3$; wherein
$X_1$ is oxygen, —O(CO)—, —(CO)O—, —O(CO)O—, —N($C_1$-$C_4$alkyl)—O—, —O—N($C_1$-$C_4$alkyl)-, thio, sulfinyl, sulfonyl, —$SO_2$N($C_1$-$C_4$alkyl)-, —N($C_1$-$C_4$alkyl)$SO_2$—, —N($C_1$-$C_2$alkoxy-$C_1$-$C_2$alkyl)$SO_2$— or —N($C_1$-$C_4$alkyl)-;

$X_2$ is a $C_1$-$C_6$alkylene, $C_3$-$C_6$alkenylene or $C_3$-$C_6$alkynylene chain which may be mono- or poly-substituted by halogen or by $X_4$, the unsaturated bonds of the chain not being bonded directly to the substituent $X_1$;

$X_3$ and $X_7$ are each independently of the other a $C_1$-$C_8$alkyl, $C_3$-$C_6$alkenyl or $C_3$-$C_6$alkynyl group which may be mono-, di- or tri-substituted by halogen, hydroxy, amino, formyl, nitro, cyano, mercapto, carbamoyl, $C_1$-$C_6$alkoxy, $C_1$-$C_6$alkoxycarbonyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl or halo-substituted $C_3$-$C_6$cycloalkyl;

or by $C_3$-$C_6$alkenyloxy, $C_3$-$C_6$alkynyloxy, $C_1$-$C_6$haloalkoxy, $C_3$-$C_6$haloalkenyloxy, cyano-$C_1$-$C_6$alkoxy, $C_1$-$C_6$alkoxy-$C_1$-$C_6$alkoxy, $C_1$-$C_6$alkoxy-$C_1$-$C_6$alkoxy-$C_1$-$C_6$alkoxy, $C_1$-$C_6$alkylthio-$C_1$-$C_6$alkoxy, $C_1$-$C_6$alkylsulfinyl-$C_1$-$C_6$alkoxy, $C_1$-$C_6$alkylsulfonyl-$C_1$-$C_6$alkoxy, $C_1$-$C_6$alkoxycarbonyl-$C_1$-$C_6$alkoxy, $C_1$-$C_6$alkoxycarbonyl, $C_1$-$C_6$alkylcarbonyl, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl; oxiranyl which may in turn be substituted by $C_1$-$C_6$alkyl; (3-oxetanyl)-oxy which may in turn be substituted by $C_1$-$C_6$alkyl; benzyloxy, benzylsulfinyl, benzylsulfonyl, $C_1$-$C_6$alkylamino, di($C_1$-$C_6$alkyl)amino, $C_1$-$C_4$alkyl-S(O)$_2$O—, di($C_1$-$C_4$alkyl)aminosulfonyl, rhodano, phenyl, phenoxy, phenylthio, phenylsulfinyl or by phenylsulfonyl; and it being possible for the phenyl- or benzyl-containing groups in turn to be substituted by one or more $C_1$-$C_6$alkyl, $C_1$-$C_6$haloalkyl, $C_1$-$C_6$alkoxy, $C_1$-$C_6$haloalkoxy, halogen, cyano, hydroxy or nitro groups; or $X_3$ and $X_7$ are phenyl which may be mono- or poly-substituted by $C_1$-$C_6$alkyl, $C_1$-$C_6$haloalkyl, $C_1$-$C_6$alkoxy, $C_1$-$C_6$haloalkoxy, halogen, cyano, hydroxy or by nitro; or $X_3$ and $X_7$ are each independently of the other $C_3$-$C_6$cycloalkyl, $C_1$-$C_6$alkoxy- or $C_1$-$C_6$haloalkyl-substituted $C_3$-$C_6$cycloalkyl, 3-oxetanyl or $C_1$-$C_6$alkyl-substituted 3-oxetanyl; or $X_3$ and $X_7$ are each independently of the other a three- to ten-membered monocyclic or annellated bicyclic ring system which may be aromatic, saturated or partially saturated and may contain from 1 to 4 hetero atoms selected from nitrogen, oxygen and sulfur, the ring system being bonded to the substituent $X_1$ or $X_5$ directly or by way of a $C_1$-$C_4$alkylene, $C_2$-$C_4$alkenylene, $C_2$-$C_4$alkynylene, —N($C_1$-$C_4$alkyl)-$C_1$-$C_4$alkylene, —S(O)—$C_1$-$C_4$alkylene or —$SO_2$-$C_1$-$C_4$alkylene group, and each ring system may contain not more than 2 oxygen atoms and not more than two sulfur atoms, and the ring system may in turn be mono-, di- or tri-substituted by $C_1$-$C_6$alkyl, $C_1$-C6haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, hydroxy, $C_1$-$C_6$haloalkoxy, $C_3$-$C_6$alkenyloxy, $C_3$-$C_6$alkynyloxy, mercapto, $C_1$-$C_6$alkylthio, $C_1$-$C_6$haloalkylthio, $C_3$-$C_6$alkenylthio, $C_3$-$C_6$haloalkenylthio, $C_3$-$C_6$-alkylthio, $C_1$-$C_3$alkoxy-$C_1$-$C_3$alkylthio, $C_1$-$C_4$alkylcarbonyl-$C_1$-$C_2$alkylthio, $C_1$-$C_4$alkoxycarbonyl-$C_1$-$C_2$alkylthio, cyano-$C_1$-$C_3$alkylthio, $C_1$-$C_6$alkylsulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_2$alkylaminosulfonyl, di($C_1$-$C_2$alkyl)aminosulfonyl, di($C_1$-$C_4$alkyl)amino, $C_1$-$C_6$carbonylamino, halogen, cyano, nitro, phenyl, benzyloxy and/or by benzylthio, it being possible for the phenyl groups in turn to be substituted on the phenyl ring by $C_1$-$C_3$alkyl, $C_1$-$C_3$haloalkyl, $C_1$-$C_3$alkoxy, $C_1$-$C_3$haloalkoxy, halogen, cyano or by nitro, and the substituents on the nitrogen in the heterocyclic ring are other than halogen; and $X_4$ and $X_8$ are each independently of the other hydroxy, $C_1$-$C_6$alkoxy, ($C_3$-$C_6$cycloalkyl)oxy, $C_1$-$C_6$alkoxy-$C_1$-$C_6$alkoxy, $C_1$-$C_6$alkoxy-$C_1$-$C_6$alkoxy-$C_1$-$C_6$alkoxy or $C_1$-$C_6$alkylsulfonyloxy;

$Ra_3$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, amino, $C_1$-$C_6$alkylamino, di($C_1$-$C_6$alkyl)amino, $C_1$-$C_4$alkylsulfonyl-N($C_1$-$C_4$alkyl)-, $C_1$-$C_6$alkylaminosulfonyl, di($C_1$-$C_6$alkyl)aminosulfonyl, cyano, halogen, $C_1$-$C_4$alkoxy-$C_1$-$C_4$alkyl, $C_1$-$C_4$alkylthio-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl,phenyl, phenylthio, phenylsulfinyl, phenylsulfonyl or phenoxy, it being possible for the phenyl groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro;

$Ra_4$ is hydrogen, $C_1$-$C_6$alkyl, hydroxy, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_1$-$C_4$alkylcarbonyloxy, $C_1$-$C_4$alkylsulfonyloxy, phenylsulfonyloxy, $C_1$-$C_4$alkylthio, $C_1$-$C_4$alkylsulfinyl, $C_1$-$C_4$alkylsulfonyl, $C_1$-$C_4$alkylamino, di($C_1$-$C_4$alkyl) amino, $C_1$-$C_4$alkoxycarbonyl, $C_1$-$C_4$haloalkyl, formyl, cyano, halogen, phenyl or phenoxy; it being possible for the phenyl-containing groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro; or $Ra_4$ is a three- to ten-membered monocyclic or with $Ra_3$ or $Ra_5$ annellated bicyclic ring system which may contain from 1 to 4 hetero atoms selected from nitrogen, oxygen and sulfur, the ring system, unless it is annellated, being bonded to the group $Q_1$ or $Q_2$ either directly or by way of a $C_1$-$C_4$alkylene, $C_1$-$C_4$alkenylene or $C_2$-$C_4$alkynylene bridge which may be interrupted by oxygen, —N($C_1$-$C_4$alkyl)-, sulfur, sulfinyl, sulfonyl or by carbonyl; and the ring system may contain not more than 2 oxygen atoms and not more than two sulfur atoms, and the ring system may in turn may be mono-, di- or tri-substituted by $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_1$-$C_6$alkoxy, $C_1$-$C_6$haloalkoxy, $C_3$-$C_6$alkenyloxy, $C_3$-$C_6$alkynyloxy, $C_1$-$C_6$alkylthio, $C_1$-$C_6$haloalkylthio, $C_3$-$C_6$alkenylthio, $C_3$-$C_6$haloalkenylthio, $C_3$-$C_6$alkynylthio, $C_1$-$C_4$alkoxy-$C_1$-$C_2$alkylthio, $C_1$-$C_4$alkylcarbonyl-$C_1$-$C_2$alkylthio, $C_1$-$C_4$alkoxycarbonyl-$C_1$-$C_2$alkylthio, cyano-$C_1$-$C_4$alkylthio, $C_1$-$C_6$alksulfinyl, $C_1$-$C_6$haloalkylsulfinyl, $C_1$-$C_6$alkylsulfonyl, $C_1$-$C_6$haloalkylsulfonyl, aminosulfonyl, $C_1$-$C_4$alkylaminosulfonyl, di($C_1$-$C_4$alkyl)aminosulfonyl, amino, $C_1$-$C_4$alkylamino, di($C_1$-$C_4$alkyl)amino, halogen, cyano, nitro, phenyl and/or by benzylthio; it being possible for phenyl and benzylthio in turn to be substituted on the phenyl ring by $C_1$-$C_3$alkyl, $C_1$-C3haloalkyl, $C_1$-$C_3$alkoxy, $C_1$-$C_3$haloalkoxy, halogen, cyano or by nitro, and substituents on the nitrogen in the heterocyclic ring are other than halogen;

$Ra_5$ is hydrogen, $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_2$-$C_6$haloalkynyl, $C_3$-$C_6$cycloalkyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkylsulfonyloxy, hydroxy, mercapto, amino, $C_1$-$C_6$alkylamino, di($C_1$-$C_6$alkyl)amino, $C_1$-$C_4$alkylsulfonylamino, $C_1$-$C_4$alkylsulfonyl-N($C_1$-$C_4$alkyl)-, $C_1$-$C_6$alkylaminosulfonyl, di($C_1$-$C_6$alkyl)aminosulfonyl, cyano, halogen, $C_1$-$C_4$alkoxy-$C_1$-$C_4$alkyl, $C_1$-$C_4$alkylthio-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl, triazolyl, phenyl, phenylthio, phenylsulfinyl, phenylsulfonyl or phenoxy; it being possible for the phenyl-containing groups to be substituted by $C_1$-$C_3$alkyl, $C_1$-$C_3$haloalkyl, $C_1$-$C_3$alkoxy, $C_1$-$C_3$haloalkoxy, halogen, cyano or by nitro; and agronomically acceptable salts/N-oxides/isomers/enantiomers of those compounds.

The alkyl groups appearing in the above substituent definitions may be straight-chain or branched and are, for example, methyl, ethyl, n-propyl, isopropyl, n-butyl, sec-butyl, isobutyl or tert-butyl. Alkoxy, alkenyl and alkynyl radicals are derived from the mentioned alkyl radicals. The alkenyl and alkynyl groups may be mono- or poly-unsaturated. Alkoxy is, for example, methoxy, ethoxy, propoxy, isopropoxy, n-butoxy, isobutoxy, sec-butoxy or tert-butoxy. Alkoxycarbonyl is, for example, methoxycarbonyl, ethoxycarbonyl, propoxycarbonyl, isopropoxycarbonyl, n-butoxycarbonyl, isobutoxycarbonyl, sec-butoxycarbonyl or tert-butoxycarbonyl; preferably methoxycarbonyl or ethoxycarbonyl.

Halogen is generally fluorine, chlorine, bromine or iodine. The same applies also to halogen in conjunction with other meanings, such as haloalkyl or halophenyl. Haloalkyl groups having a chain length of from 1 to 6 carbon atoms are, for example, fluoromethyl, difluoromethyl, chlorodifluoromethyl, trifluoromethyl, chloromethyl, dichloromethyl, trichloromethyl, 2,2,2-trifluoroethyl, 1-fluoroethyl, 2-fluoroethyl, 2-chloroethyl, 2-fluoroprop-2-yl, pentafluoroethyl, 1,1-difluoro-2,2,2-trichloroethyl, 2,2,3,3-tetrafluoroethyl and 2,2,2-trichloroethyl, pentafluoroethyl, heptafluoro-n-propyl and perfluoro-n-hexyl.

Alkenyl and alkynyl groups may be mono- or poly-unsaturated, so that alkyl, alkenyl and alkynyl chains having one or more double or triple bonds are also included. Alkenyl is, for example, vinyl, allyl, isobuten-3-yl, $CH_2=CH-CH_2-CH=CH-$, $CH_2=CH-CH_2-CH_2-CH=CH-$ or $CH_3-CH=CH-CH_2-CH=CH-$. A preferred alkynyl is, for example, propargyl, and a preferred allenyl is $CH_2=C=CH_2-$.

An alkylene chain may also be substituted by one or more $C_1$-$C_3$alkyl groups, especially by methyl groups. Such alkylene chains and alkylene groups are preferably unsubstituted. The same applies also to all groups containing $C_3$-$C_6$cycloalkyl, $C_3$-$C_5$oxacycloalkyl, $C_3$-$C_5$thiacycloalkyl, $C_3$-$C_4$dioxacycloalkyl, $C_3$-$C_4$dithiacycloalkyl or $C_3$-$C_4$oxathiacycloalkyl, which occur, for example, also as part of oxygen- and sulfur-containing heterocyclic ring systems of the radicals $Ra_1$ and $Ra_2$.

A $C_1$-$C_4$alkylene, $C_1$-$C_4$alkenylene or $C_2$-$C_4$alkynylene chain which may be interrupted by oxygen, $-N(C_1$-$C_4$alkyl)-, sulfur, sulfinyl or by sulfonyl, or in $X_2$ or $X_6$ in the meaning of a $C_1$-$C_6$alkylene, $C_3$-$C_6$alkenylene or $C_3$-$C_6$alkynylene chain which may be mono- or poly-substituted by halogen or by $X_4$ or $X_8$, and wherein the unsaturated bonds of the chain are not bonded directly to the substituent $X_1$ or $X_5$, is to be understood as being, for example $-CH_2-$, $-CH_2CH_2-$, $-CH_2CH_2CH_2-$, $-CH_2CH_2CH_2CH_2-$, $-CH(CH_3)-$, $-CH_2CH(CH_3)-$, $-CH_2CH(CH_3)CH_2-$, $-CH_2CH(Cl)CH_2-$, $-CH_2CH(OCH_3)CH_2-$, $-CH_2O-$, $-OCH_2-$, $-CH_2OCH_2-$, $-OCH_2CH_2-$, $-OCH_2CH_2CH_2-$, $-CH_2OCH_2CH_2-$, $-CH_2OCH(CH_3)CH_2-$, $-SCH_2-$, $-SCH_2CH_2-$, $-SCH_2CH_2CH_2-$, $-CH_2S-$, $-CH_2SCH_2-$, $-CH_2S(O)CH_2-$, $-CH_2SO_2CH_2-$, $-CH_2SCH_2CH_2-$, $-CH_2S(O)CH_2CH_2-$, $-CH_2SO_2CH_2CH_2-$, $-CH_2SO_2NH-$, $-CH_2N(CH_3)SO_2CH_2CH_2-$, $-N(SO_2Me)CH_2CH_2-$, $-CH_2C(O)NH-$ or $-CH_2NHC(O)CH_2-$. A $C_2$-$C_4$alkenylene chain which may be interrupted by oxygen is accordingly to be understood as being, for example, $-CH=CH-CH_2-$, $-CH=CH-CH_2CH_2-$ or $-CH=CHCH_2OCH_2-$, and a $C_2$-$C_4$alkynylene chain which may be interrupted by oxygen is to be understood as being, for example, $-C\equiv C-$, $-C\equiv CCH_2-$, $-C\equiv CCH_2O-$, $-C\equiv CCH_2OCH_2-$ or $-OC\equiv CCH_2-$.

A three- to ten-membered mono- or bi-cyclic ring system $Ra_1$ or $Ra_2$, which may be interrupted once or up to three times selected from oxygen, sulfur, S(O), $SO_2$, N($Ra_6$), carbonyl and C(=NO$Ra_7$) and which is bonded to the carbon atom of the substituent $A_1$ or to the group $Q_1$ or $Q_2$ either directly or by way of a $C_1$-$C_4$alkylene, $C_1$-$C_4$alkenylene or $C_2$-$C_4$alkynylene bridge which may be interrupted by oxygen, $-N(C_1$-$C_4$alkyl)-, sulfur, sulfinyl or by sulfonyl, is to be understood as being, for example, 1-methyl-1H-pyrazol-3-yl, 1-ethyl-1H-pyrazol-3-yl, 1-propyl-1H-pyrazol-3-yl, 1H-pyrazol-3-yl, 1,5-dimethyl-1H-pyrazol-3-yl, 4-chloro-1-methyl-1H-pyrazol-3-yl, 1H-pyrazol-1-yl, 3-methyl-1H-pyrazol-1-yl, 3,5-dimethyl-1H-pyrazol-1-yl, 3-isoxazolyl, 5-methyl-3-isoxazolyl, 3-methyl-5-isoxazolyl, 5-isoxazolyl, 1H-pyrrol-2-yl, 1-methyl-1H-pyrrol-2-yl, 1H-pyrrol-1-yl, 1-methyl-1H-pyrrol-3-yl, 2-furyl, 5-methyl-2-furyl, 3-furyl, 5-methyl-2-thienyl, 2-thienyl, 3-thienyl, 1-methyl-1H-imidazol-2-yl, 1H-imidazol-2-yl, 1-methyl-1H-imidazol-4-yl, 1-methyl-1H-imidazol-5-yl, 4-methyl-2-oxazolyl, 5-methyl-2-oxazolyl, 2-oxazolyl, 2-methyl-5-oxazolyl, 2-methyl-4-oxazolyl, 4-methyl-2-thiazolyl, 5-methyl-2-thiazolyl, 2-thiazolyl, 2-methyl-5-thiazolyl, 2-methyl-4-thiazolyl, 3-methyl-4-isothiazolyl, 3-methyl-5-isothiazolyl, 5-methyl-3-isothiazolyl, 1-methyl-1H-1,2,3-triazol-4-yl, 2-methyl-2H-1,2,3-triazol-4-yl, 4-methyl-2H-1,2,3-triazol-2-yl, 1-methyl-1H-1,2,4-triazol-3-yl, 1,5-dimethyl-1H-1,2,4-triazol-3-yl, 3-methyl-1H-1,2,4-triazol-1-yl, 5-methyl-1H-1,24-triazol-1-yl, 4,5-dimethyl-4H-1,2,4-triazol-3-yl, 4-methyl-4H-1,2,4-triazol-3-yl, 4H-1,2,4-triazol-4-yl, 5-methyl-1,2,3-oxadiazol-4-yl, 1,2,3-oxadiazol-4-yl, 3-methyl-1,2,4-oxadiazol-5-yl, 5-methyl-1,2,4-oxadiazol-3-yl, 4-methyl-3-furazanyl, 3-furazanyl, 5-methyl-1,2,4-oxadiazol-2-yl, 5-methyl-1,2,3-thiadiazol-4-yl, 1,2,3-thiadiazol-4-yl, 3-methyl-1,2,4-thiadiazol-5-yl, 5-methyl-1,2,4-thiadiazol-3-yl, 4-methyl-1,2,5-thiadiazol-3-yl, 5-methyl-1,3,4-thiadiazol-2-yl, 1-methyl-1H-tetrazol-5-yl, 1H-tetrazol-5-yl, 5-methyl-1H-tetrazol-1-yl, 2-methyl-2H-tetrazol-5-yl, 2-ethyl-2H-tetrazol-5-yl, 5-methyl-2H-tetrazol-2-yl, 2H-tetrazol-2-yl, 2-pyridyl, 6-methyl-2-pyridiyl, 4-pyridyl, 3-pyridyl, 6-methyl-3-pyridazinyl, 5-methyl-3-pyridazinyl, 3-pyridazinyl, 4,6-dimethyl-2-pyrimidinyl, 4-methyl-2-pyrimidinyl, 2-pyrimidinyl, 2-methyl-4-pyrimidinyl, 2-chloro-4-pyrimidinyl, 2,6-dimethyl-4-pyrimidinyl, 4-pyrimidinyl, 2-methyl-5-pyrimidinyl, 6-methyl-2-pyrazinyl, 2-pyrazinyl, 4,6-dimethyl-1,3,5-triazin-2-yl, 4,6-dichloro-1,3,5-triazin-2-yl, 1,3,5-triazin-2-yl, 4-methyl-1,3,5-triazin-2-yl, 3-methyl-1,2,4-triazin-5-yl, 3-methyl-1,2,4-triazin-6-yl,

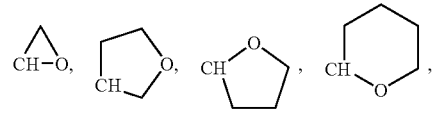

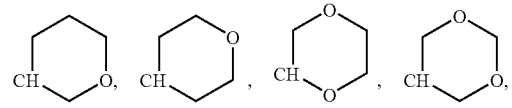

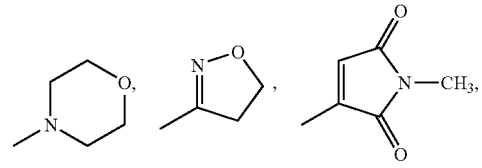

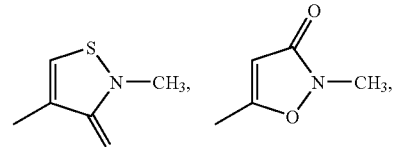

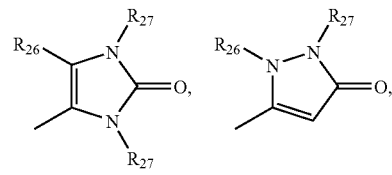

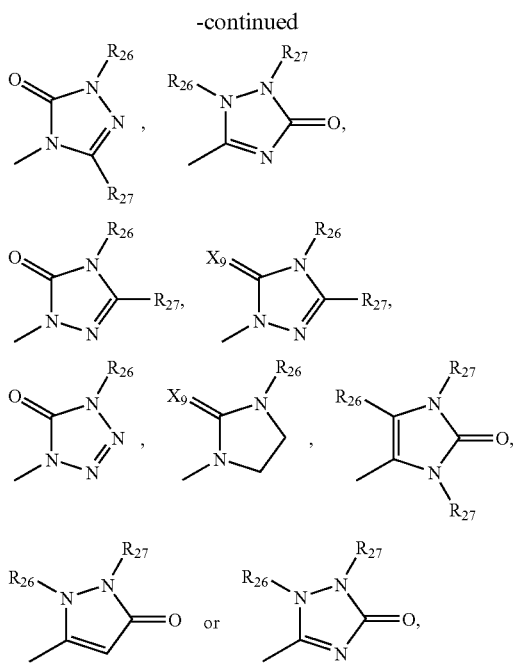

wherein each $R_{26}$ is methyl, each $R_{27}$ independently is hydrogen, $C_1$-$C_3$alkyl, $C_1$-$C_3$alkoxy, $C_1$-$C_3$alkylthio or trifluoromethyl, and $X_9$ is oxygen or sulfur.

A further annellated (fused-on), monocyclic or bicyclic ring system which is formed, for example, by two adjacent substituents $Ra_1$ and $Ra_2$ or $Ra_1$ and $Ra_5$ and which is interrupted once or up to three times selected from oxygen, sulfur, S(O), SO$_2$, —N(Ra$_6$)—, carbonyl and C(=NORa$_7$) and which may be additionally substituted by one or more substituents is to be understood as being, for example, an annellated, bidentate ring system of formula

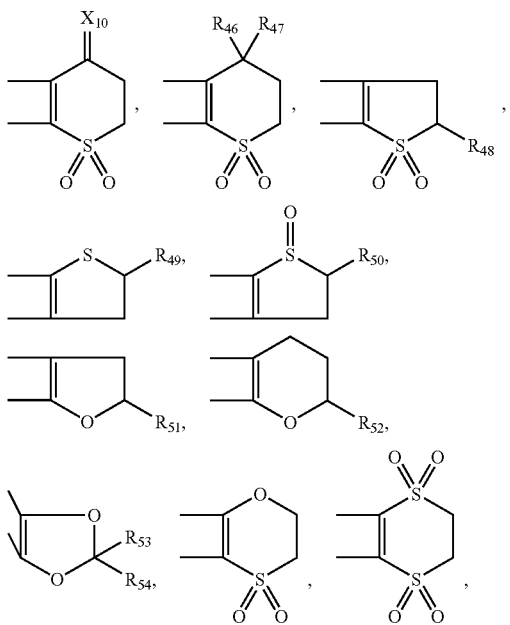

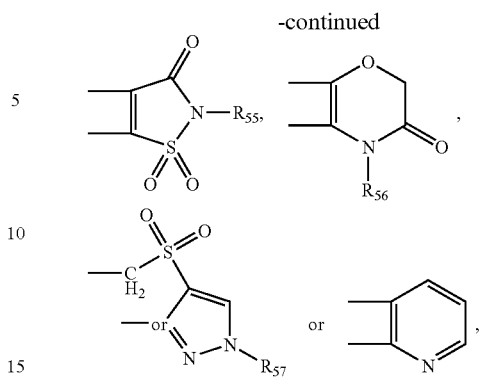

wherein especially $R_{46}$ is hydrogen, halogen, $C_1$-$C_4$alkyl, $C_1$-$C_4$haloalkyl, $C_1$-$C_4$alkoxy or $C_1$-$C_4$alkylthio; $R_{47}$ is hydrogen, halogen, $C_1$-$C_4$alkyl or $C_1$-$C_4$alkoxy; $R_{50}$, $R_{51}$, $R_{52}$, $R_{53}$, $R_{54}$, $R_{55}$, $R_{56}$, $R_{57}$, $R_{58}$ and $R_{59}$ are each independently of the others hydrogen $C_1$-$C_4$alkyl; and $X_{10}$ is oxygen or NOR$_{59}$.

A heteroaryl group Y substituted at least in the ortho position is to be understood as being especially a 5- or 6-membered aromatic heteroaryl group as defined hereinbefore which is, in addition, substituted once or up to three times by substituents selected from the meanings of $Ra_1$, $Ra_2$, $Ra_3$ and $Ra_4$ and $Ra_5$ at the nitrogen and/or at the carbon atoms.

Using the process according to the invention it is possible, especially advantageously, to prepare the cyclohexanedione herbicides described in WO 00/15615, WO 00/37437, WO 01/66522 and WO 01/94339.

Compounds of formula I that are highly suitable for preparation using the process according to the invention are those wherein
$R_1$ and $R_2$ are hydrogen;
Q is $Q_1$, wherein $A_4$ is CRa$_1$ or N—(O)$_p$;
p is 0;
$Ra_1$ is hydrogen, $C_1$-$C_6$alkyl, hydroxy, $C_1$-$C_6$alkoxy, $C_1$-$C_6$haloalkoxy, $C_3$-$C_6$alkenyloxy, $C_3$-$C_6$haloalkenyloxy, $C_3$-$C_6$alkynyloxy, $C_1$-$C_4$alkoxy-$C_1$-$C_2$alkoxy, $C_1$-$C_4$alkoxy-$C_1$-$C_2$alkoxy-$C_1$-$C_2$alkoxy, ($C_3$-$C_6$cycloalkyl)-$C_1$-$C_2$alkoxy, (1,3-dioxolan-2-yl)-$C_1$-$C_2$alkoxy, (tetrahydro-furan-2-yl)-$C_1$-$C_2$alkoxy, (tetrahydro-furan-3-yl)oxy, (oxetan-3-yl)oxy, ($C_3$-$C_6$cycloalkyl) oxy, $C_1$-$C_4$alkylsulfonyloxy, $C_1$-$C_4$alkylthio, C1-$C_4$alkylsulfonyl, $C_1$-$C_4$alkylamino, di($C_1$-$C_4$alkyl) amino, $C_1$-$C_2$alkoxyethylamino, $C_1$-$C_2$alkoxyethyl-(N-methyl)amino, morpholino, $C_1$-$C_4$alkylcarbonylaminoethoxy, $C_1$-$C_4$alkoxycarbonyl, hydroxymethyl, $C_1$-$C_6$alkoxymethyl, $C_1$-$C_6$haloalkoxymethyl, $C_3$-$C_6$alkenyloxymethyl, $C_3$-$C_6$haloalkenyloxymethyl, $C_3$-$C_6$alkynyloxymethyl, $C_1$-$C_4$alkoxy-$C_1$-$C_2$alkoxymethyl, ($C_3$-$C_6$cycloalkyl) methoxymethyl, (1,3-dioxolan-2-yl) methoxymethyl, (tetrahydro-furan-2-yl)methoxymethyl, (tetrahydro-furan-3-yl)oxymethyl, (oxetan-3-yl)oxymethyl, ($C_3$-$C_6$cycloalkyl) oxymethyl, $C_1$-$C_4$alkylcarbonylamino-$C_1$-$C_2$alkoxy, $C_1$-$C_4$haloalkyl, cyano, halogen, phenyl or benzyloxy, it being possible for a phenyl-containing group in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro;
$Ra_2$ is $C_1$-$C_6$alkyl, $C_1$-$C_6$haloalkyl, $C_2$-$C_6$alkenyl, $C_2$-$C_6$haloalkenyl, $C_2$-$C_6$alkynyl, $C_3$-$C_6$cycloalkyl, halo- or $C_1$-$C_2$alkoxymethyl-substituted $C_3$-$C_6$cycloalkyl, $C_1$-$C_6$alkoxy, $C_3$-$C_6$alkenyloxy, $C_3$-$C_6$alkynyloxy, $C_1$-$C_6$haloalkoxy, $C_3$-$C_6$haloalkenyloxy, $C_1$-$C_4$alkoxy-$C_1$-$C_4$alkoxy, $C_1$-$C_4$alkoxy-$C_1$-$C_4$alkoxy, $C_1$-$C_4$alkylthio-$C_1$-$C_4$alkoxy, $C_1$-$C_4$alkylsulfinyl-$C_1$-$C_4$alkoxy, $C_1$-$C_4$alkylsulfonyl-$C_1$-$C_4$alkoxy, $C_1$-$C_4$alkoxycarbonyl-$C_1$-$C_4$alkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkylaminosulfonyl, di($C_1$-$C_6$alkyl)aminosulfonyl, $C_1$-$C_4$alkylsulfonyloxy, $C_1$-$C_4$haloalkylsulfonyloxy, $C_1$-$C_4$alkylsulfonylamino, $C_1$-$C_4$alkylsulfonyl-N($C_1$-$C_4$-alkyl), cyano, halogen, hydroxy-$C_1$-$C_4$alkyl, $C_1$-$C_4$alkoxy-$C_1$-$C_4$alkyl, $C_1$-$C_4$alkylthio-$C_1$-$C_4$alkyl, $C_1$-$C_4$alkylsulfinyl-$C_1$-$C_4$alkyl, $C_1$-$C_4$alkylsulfonyl-$C_1$-$C_4$alkyl, cyano-$C_1$-$C_4$alkyl, $C_1$-$C_6$alkylcarbonyloxy-$C_1$-$C_4$alkyl, $C_1$-$C_4$alkoxycarbonyl-$C_1$-$C_4$alkyl, $C_1$-$C_4$alkoxycarbonyloxy-$C_1$-$C_4$alkyl, phenoxy-$C_1$-$C_4$alkyl, benzyloxy-$C_1$-$C_4$alkyl, benzoyloxy-$C_1$-$C_4$alkyl, benzyloxy, benzylthio, phenoxy or phenylthio, it being possible for the phenyl-containing groups in turn to be substituted by $C_1$-$C_3$alkyl, $C_1$-$C_3$haloalkyl, $C_1$-$C_3$alkoxy, $C_1$-$C_3$haloalkoxy, halogen, cyano or by nitro; or $Ra_2$ is the group -$X_1$-$X_3$ or the group -$X_2$-$X_1$-$X_3$, wherein $X_1$, $X_2$ and $X_3$ are as defined hereinbefore; or $Ra_3$ is hydrogen; or $Ra_4$ is hydrogen or methyl; or $Ra_5$ is $C_1$-$C_6$haloalkyl, $C_2$-$C_6$haloalkenyl, $C_1$-$C_6$alkoxy, $C_1$-$C_6$haloalkoxy, $C_1$-$C_6$alkylthio, $C_1$-$C_6$alkylsulfinyl, $C_1$-$C_6$alkylsulfonyl, $C_1$-$C_6$haloalkylthio, $C_1$-$C_6$haloalkylsulfinyl, $C_1$-$C_6$haloalkylsulfonyl, $C_1$-$C_6$alkylsulfonyloxy, $C_1$-$C_4$alkylaminosulfonyl, di($C_1$-$C_4$alkyl)aminosulfonyl, $C_1$-$C_4$alkylsulfonylamino, $C_1$-$C_4$alkylsulfonyl-N($C_1$-$C_4$alkyl)-, cyano, halogen, $C_1$-$C_4$alkoxymethyl, $C_1$-$C_4$alkylthiomethyl, $C_1$-$C_4$alkylsulfinylmethyl, $C_1$-$C_4$alkylsulfonylmethyl or 1H-1,2,4-triazol-1-yl.

Compounds of formula I that are especially highly suitable for preparation using the process according to the invention are those wherein $R_2$ and $R_5$ together are ethylene;

$R_1$ and $R_6$ are hydrogen;

$A_2$ is $C(R_3R_4)_n$, wherein $R_3$ and $R_4$ are hydrogen and n is 1.

The process according to the invention is explained in greater detail by the following Examples.

Reaction Step a):

A preferred bromination agent is oxalyl bromide. A suitable chlorination agent is thionyl chloride, oxalyl chloride or phosgene. The reaction may be carried out in the presence of a base such as, for example, a tertiary amine or heterocyclic amine, or an inorganic carbonate or hydrogen carbonate. The reaction may furthermore be carried out without the addition of base in the presence of a catalytic amount of a tertiary amide such as, for example, dimethylformamide. The reaction of the compound of formula II with the compound of formula III is carried out in the presence of a base such as, for example, a tertiary amine or heterocyclic amine, or an inorganic carbonate and a catalytic amount of a tertiary amide such as, for example, dimethylformamide, $R_9$ preferably being methyl. Reaction Step a) may be carried out at temperatures from 0° C. to 100° C.

Suitable solvents are ethers, hydrocarbons or chlorinated hydrocarbons.

Compounds of formula 11 are known; they are commercially available in some cases or can be prepared by known methods.

The intermediates of formula IV

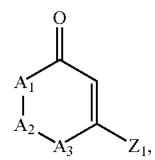

(IV)

wherein $A_1$, $A_2$ and $A_3$ are as defined for formula I and $Z_1$ is chlorine, bromine or $OSO_2R_9$, $R_9$ being as defined for formula III, are novel and were developed specifically for the present process, and the present invention accordingly also relates thereto.

Especially preferred intermediates are the compounds of formulae IVa and IVb

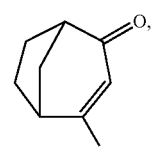

(IVa)

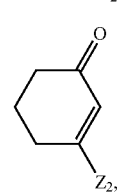

(IVb)

wherein $Z_2$ is chlorine, bromine or $OSO_2R_9$, $R_9$ being as defined for formula III but preferably being methyl.

Reaction Step b):

Reaction Step b) is carried out in the absence of water and in the presence of a base, for example a tertiary amine, preferably triethylamine or diisopropylethylamine. The reaction is preferably carried out in the presence of a solvent such as a hydrocarbon, acetonitrile, ether or dipolar aprotic solvent. When $Z_1$ is $OSO_2R_9$, the reaction is preferably carried out in chlorobenzene, toluene, acetonitrile or tetrahydrofuran. For activation of the leaving group $Z_1$, the presence of a catalyst such as, for example, a Lewis acid such as $ZnCl_2$ or $AgClO_4$ is advantageous. When $Z_1$ is chlorine or bromine, the reaction is preferably carried out in the presence of acetonitrile, toluene, xylene or chlorobenzene as solvent. When $Z_1$ is $OSO_2R_9$, the reaction temperatures are from 0° C. to 150° C., preferably from 0° C. to 100° C. When $Z_1$ is chlorine or bromine, the reaction is preferably carried out at temperatures of from 80° C. to 130° C.

Reaction Step c):

In an especially preferred embodiment of the process according to the invention, the reaction according to Reaction Step c) is carried out without isolation of intermediates, that is to say the compound of formula VI obtained according to Reaction Step b) is treated in situ with cyanide ions in the presence of a base.

The cyanide ions are preferably used in amounts of from 0.01% to 15%. The reaction is preferably carried out at a temperature of from 50° C. to 150° C., especially at from 50° C. to 100° C., in the absence of water and in the presence of a base, for example from 0.1 to 2.5 equivalents of triethylamine, or Hünig's base.

A suitable cyanide ion source is, for example, sodium cyanide, potassium cyanide, copper(I) cyanide, acetone cyanohydrin or trimethylsilyl cyanide, preferably potassium cyanide. Suitable solvents for Reaction Step c) are, for example, hydrocarbons, acetonitriles, ethers, chlorinated hydrocarbons and dipolar aprotic solvents. Such enol ester rearrangements are described, for example, in EP-A-0 186 117.

In a very especially preferred embodiment of the process according to the invention, Reaction Steps a), b) and c) are carried out without isolation of intermediates, in the form of a one-pot reaction. The possibility of carrying out the process according to the invention in a one-pot reaction constitutes a considerable advantage especially for large-scale application.

The process according to the invention will be explained in greater detail in the following Preparation Examples:

EXAMPLE P1

Preparation of 3-bromobicyclo[3.2.1]oct-2-en-1-one

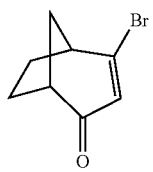

To a solution of 5 g (34.4 mmol) of bicyclo[3.2.1]octane-2,4-dione (preparation in accordance with JP 10265441 A2) in 50 ml of dichloromethane there are added, in succession, with stirring, 0.05 ml of dimethylformamide and then, over the course of 15 minutes, 8.9 g (41.3 mmol) of oxalyl bromide in portions, during which gas is evolved. The exothermic reaction is controlled using a water bath. The resulting light-brown solution is stirred for one hour at ambient temperature. The reaction mixture is then washed with 50 ml of 1M sodium hydrogen carbonate solution, a high degree of foaming being observed, and is then dried using magnesium sulfate. After removal of the solvent in vacuo, 4.8 g (56% of theory) of 3-bromobicyclo[3.2.1]oct-2-en-1-one are obtained in the form of a dark-brown oil.

MS: 202 (M$^+$ $^{81}$Br isotope), 200 (M$^+$ $^{79}$Br isotope), 161, 159, 133, 131, 121, 91, 77, 65, 51, 39

$^1$H NMR (CDCl$_3$): 1.60-1.70 (m, 2H), 1.85-1.95 (m, 1H), 1.95-2.05 (m, 1H), 2.10-2.20 (m, 2H), 2.95 (m, 1H), 3.20 (m, 1H), 6.20 (s, 1H).

EXAMPLE P2

3-Chlorobicyclo[3.2.1]oct-2-en-1-one

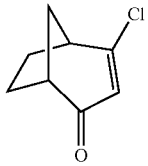

To a solution of 4.8 g (32.8 mmol) of bicyclo[3.2.1]octane-2,4-dione in 50 ml of dichloromethane there are added, in succession, with stirring, 0.05 ml of dimethylformamide and then, over the course of 30 minutes, 5 g (39.4 mmol) of oxalyl chloride in portions, during which gas is evolved. The exothermic reaction is controlled using a water bath. The resulting red-brown solution is stirred for 30 minutes at ambient temperature. The reaction mixture is divided into two equal portions. One portion of the reaction mixture is then washed with 50 ml of 1M sodium hydrogen carbonate solution, a high degree of foaming being observed. After removal of the solvent in vacuo, 1.9 g (70% of theory) of 3-chlorobicyclo[3.2.1]oct-2-en-1-one are obtained in the form of a brown oil.

MS: 158 (M$^+$ $^{37}$Cl isotope), 156 (M$^+$ $^{35}$Cl isotope), 117, 115, 91, 87, 77, 65, 51, 39

$^1$H NMR (CDCl$_3$): 1.60-1.70 (m, 2H), 1.80-1.95 (m, 1H), 2.00-2.10 (m, 1H), 2.15-2.25 (m, 2H), 2.95 (m, 1H), 3.05 (m, 1H), 6.00 (s, 1H)

EXAMPLE P3

Preparation of 4-oxo-bicyclo[3.2.1]oct-2-en-2-yl-methanesulfonic acid ester

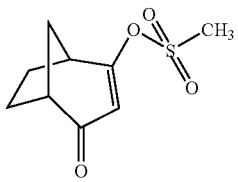

13.82 g (100 mmol) of bicyclo[3.2.1]octane-2,4-dione, 11.46 g (100 mmol) of methanesulfonyl chloride and 15.18 g (150 mmol) of triethylamine are heated in 100 ml of chloroform at a temperature of from 60 to 65° C. with stirring for 24 hours. 15.3 g of 4-oxo-bicyclo-[3.2.1]oct-2-en-2-yl-methanesulfonic acid ester in the form of a brown, gum-like product are obtained, which can be used for the next Reaction Step without further purification.

$^1$H NMR (CDCl$_3$): 1.6-1.75 (m, 2H), 1.9-2.2 (m, 4H), 2.9-3.0 (m, 2H, bridgehead), 3.25 (s, 3H, CH$_3$SO$_3$—), 5.8 (s, 1H, vinyl).

EXAMPLE P4

Preparation of 2-phenylcarbonyloxy-4-oxo-bicyclo[3.2.1]oct-2-ene

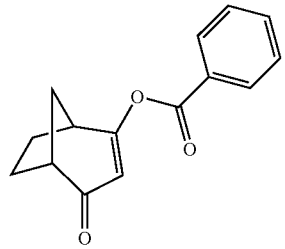

2.165 g (10 mmol) of 4-oxo-bicyclo[3.2.1]oct-2-en-2-yl-methanesulfonic acid ester (Preparation Example P3), 1.34 g (11 mmol) of benzoic acid and 1.52 g (15 mmol) of triethylamine in 20 ml of chlorobenzene are heated with stirring for 8 hours. The cooled reaction mixture is then washed with 5% aqueous sulfuric acid and 5% aqueous sodium hydroxide. The organic phase is dried over sodium sulfate and concentrated to dryness by evaporation in vacuo. 2.99 g of 2-phenylcarbonyloxy-4-oxo-bicyclo[3.2.1]oct-2-ene are obtained in the form of a brown oil.

$^1$H NMR (CDCl$_3$): 1.65-1.8 (m, 2H), 2.0-2.4 (m, 4H), 2.95-3.1 (m, 2H, bridgehead), 5.85 (s, 1H, vinyl), 6.95-7.05 (m, 2H, aryl), 7.1-7.2 (m, 1H, aryl), 8.05-8.15 (m, 2H, aryl).

EXAMPLE P5

Preparation of 3-(2-nitro-4-methylsulfonyl-phenyl-carbonyloxy)-cyclohex-2-en-1-one

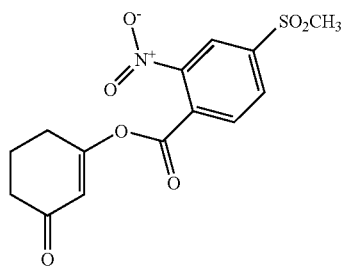

To a mixture of 157 mg (1.15 mmol) of 3-chlorocyclohex-2-en-1-one (prepared as described in Synthesis (1974), (1), 47-8), 16 mg (0.12 mmol) of ZnCl$_2$, 297 mg (1.15 mmol) of 2-nitro-4-methylsulfonybenzoic acid and 3 ml of anhydrous acetonitrile there are added dropwise, under a nitrogen atmosphere, over the course of 15 minutes, 166 mg (1.27 mmol) of diisopropylethylamine. A further 2 ml of acetonitrile are then added and, with stirring, the reaction mixture is maintained at a temperature of 45° C. for 18 hours in an oil bath. The reaction mixture is then heated up again and maintained at reflux temperature for 40 hours.

The reaction mixture is then brought to ambient temperature and the solvent is removed in vacuo. 25 ml of dichloromethane and 0.35 g of 36% hydrochloric acid in 5 ml of water are then added and the phases are separated. The organic phase is washed twice with 10 ml of water, dried using magnesium sulfate and concentrated in vacuo. 197 mg of 3-(2-nitro-4-methylsulfonyl-phenylcarbonyloxy)-cyclohex-2-en-1-one are obtained in the form of a brown oil.

$^1$H NMR (CDCl$_3$): 2.10-2.20 (m, 2H), 2.45-2.50 (m, 2H), 2.70-2.75 (m, 2H), 3.20 (s, 3H, C$\underline{H}_3$SO$_2$), 6.10 (s, 1H, C=C$\underline{H}$), 8.00 (d, 1H, ar. $\underline{H}$), 8.35 (d, 1H, ar. $\underline{H}$), 8.65 (s, 1H, ar. $\underline{H}$).

EXAMPLE P6

Preparation of 3-(2-methoxyethoxymethyl-6-trifluoromethyl-pyridin-3-ylcarbonyloxy)-cyclohex-2-en-1-one

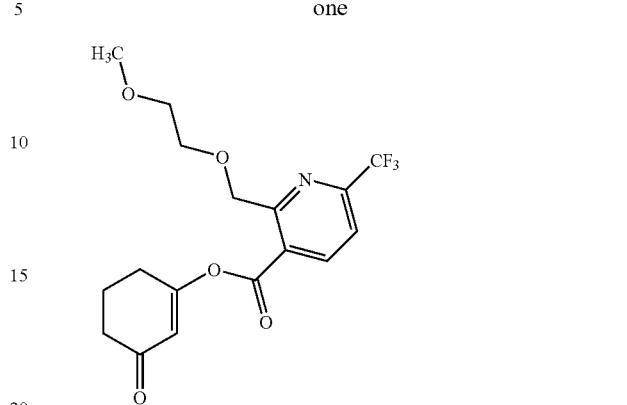

To a mixture of 157 mg (1.15 mmol) of 3-chlorocyclohex-2-en-1-one, 16 mg (0.12 mmol) of ZnCl$_2$, 324 mg (1.15 mmol) of 2-methoxyethoxymethyl-6-trifluoromethylnicotinic acid (preparation described in WO 2001094339) and 2 ml of toluene there are added dropwise, under a nitrogen atmosphere, over the course of 15 minutes, 166 mg (1.27 mmol) of diisopropylethylamine. A further 2 ml of toluene are then added and, with stirring, the reaction mixture is maintained under moderate reflux for 18 hours in an oil bath. The reaction mixture is then brought to ambient temperature and 30 ml of dichloromethane and 20 ml of water are added. The organic phase is separated off and washed twice with 0.1M hydrochloric acid (20 ml) and twice with water (10 ml). After drying using magnesium sulfate and concentration in vacuo, 226 mg of 3-(2-methoxyethoxymethyl-6-trifluoromethyl-pyridin-3-ylcarbonyloxy)-cyclohex-2-en-1-one are obtained in the form of an orange-brown oil.

MS: 373 (M$^+$), 354, 328, 262, 230, 202, 187, 159, 139, 109, 95, 59, 45.

$^1$H NMR (CDCl$_3$): 2.10-2.20 (m, 2H), 2.45-2.50 (m, 2H), 2.70-2.75 (m, 2H), 3.35 (s, 3H, C$\underline{H}_3$O), 3.50 (CH$_2$C$\underline{H}_2$O), 3.70 (OC$\underline{H}_2$CH$_2$), 5.00 (s, 2H, ar. C$\underline{H}_2$), 6.10 (s, 1, C=C$\underline{H}$), 7.75 (d, 1H, ar. $\underline{H}$), 8.30 (d, 1H, ar. $\underline{H}$).

EXAMPLE P7

Preparation of 4-(2-methoxyethoxymethyl-6-trifluoromethyl-pyridin-3-yl-carbonyloxy)-bicyclo[3.2.1]oct-3-en-2-one

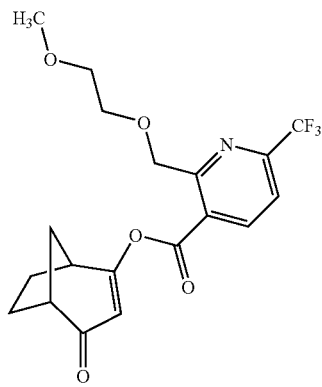

A mixture of 200 mg (1.15 mmol) of 4-chlorobicyclo[3.2.1]oct-3-en-2-one, (Preparation Example P2) 16 mg (0.12 mmol) of $ZnCl_2$, 324 mg (1.15 mmol) of 2-methoxyethoxymethyl-6-trifluoromethylnicotinic acid, 166 mg (1.27 mmol) of diisopropylethylamine and 5 ml of toluene is stirred under a nitrogen atmosphere at room temperature until a clear brown solution having a white sediment is formed. The reaction mixture is then maintained under moderate reflux for 26 hours in an oil bath, with stirring. The reaction mixture is then cooled to ambient temperature and 30 ml of dichloromethane are added. The solution is then washed twice with water (20 ml each time) and then twice with 0.1M hydrochloric acid (20 ml each time) and again twice with water (15 ml each time). After drying the organic solution using magnesium sulfate and concentrating in vacuo, 284 mg of 4-(2-methoxyethoxymethyl-6-trifluoromethyl-pyridin-3-ylcarbonyloxy)-bicyclo[3.2.1]oct-3-en-2-one are obtained in the form of a brown oil.

MS: 399(M+), 380, 354, 262, 230, 204, 187, 159, 139, 121, 91.

$^1$H NMR (CDCl$_3$): 1.65-1.75 (m, 2H), 2.05-2.30 (m, 4H), 3.00 (br t, 1H), 3.10 (br s, 1H), 3.35 (s, 3H, OC$\underline{H}_3$), 3.50 (m, 2H, CH$_2$C$\underline{H}_2$O), 3.70 (m, 2H, OC$\underline{H}_2$CH$_2$), 5.00 (s, 2H, ar. C$\underline{H}_2$), 5.90 (s, 1H, C=C$\underline{H}$), 7.75 (d, 1H, ar. $\underline{H}$), 8.30 (d, 1H, ar. $\underline{H}$).

EXAMPLE P8

Preparation of 4-(4-chlorophenyl-carbonyloxy)-bicyclo[3.2.1]oct-3-en-2-one

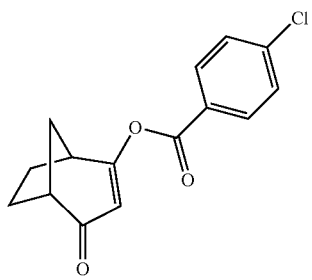

A mixture of 500 mg of 4-chlorobicyclo[3.2.1]oct-3-en-2-one (Preparation Example P2), 440 mg of $ZnCl_2$, 400 mg of 4-chlorobenzoic acid, 1.05 g of diisopropylethylamine and 5 ml of toluene is stirred at room temperature under a nitrogen atmosphere at reflux temperature for 6 hours. After cooling, the reaction mixture is then diluted with dichloromethane and washed with 5% aqueous sulfuric acid and 5% aqueous sodium hydroxide. After concentration of the organic phase to dryness by evaporation, 0.6 g of 4-(4-chlorophenyl-carbonyloxy)-bicyclo[3.2.1]oct-3-en-2-one is obtained.

$^1$H NMR (CDCl$_3$): 1.65-1.8 (m, 2H), 2.0-2.4 (m, 4H), 2.95-3.1 (m, 2H, bridgehead), 5.85 (s, 1H, vinyl), 6.95-7.05 (m, 2H, aryl), 8.0-8.1 (m, 2H, aryl).

EXAMPLE P9

Preparation of 4-phenyl-carbonyloxy-bicyclo[3.2.1]oct-3-en-2-one

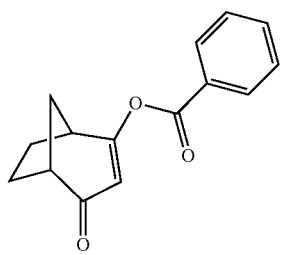

A mixture of 500 mg of 4-chlorobicyclo[3.2.1]oct-3-en-2-one (Preparation Example P2), 440 mg of $ZnCl_2$, 400 mg of 4-benzoic acid, 1.05 g of diisopropylethylamine and 5 ml of toluene is stirred at room temperature under a nitrogen atmosphere at reflux temperature for 8 hours. After cooling, the reaction mixture is then diluted with dichloromethane and washed with 10% aqueous sulfuric acid. After concentration of the organic phase to dryness by evaporation, 0.4 g of 4-phenyl-carbonyloxy-bicyclo[3.2.1]oct-3-en-2-one is obtained.

$^1$H NMR (CDCl$_3$): 1.65-1.8 (m, 2H), 2.0-2.4 (m, 4H), 2.95-3.1 (m, 2H, bridgehead), 5.85 (s, 1H, vinyl), 6.95-7.05 (m, 2H, aryl), 7.1-7.2 (m, 1H, aryl), 8.05-8.15 (m, 2H, aryl).

EXAMPLE P10

Preparation of 4-(2-methoxyethoxymethyl-6-trifluoromethyl-pyridin-3-yl-carbonyloxy)-bicyclo[3.2.1]oct-3-en-2-one

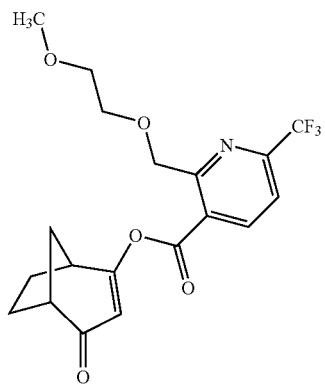

A mixture of 27 g of a 6.2% solution of 4-bromobicyclo[3.2.1]oct-3-en-2-one (Preparation Example P1) in chlorobenzene, 110 mg of $ZnCl_2$, 2.34 g of 2-methoxyethoxymethyl-6-trifluoromethylnicotinic acid and 1.2 g of Hünig's base is stirred at room temperature under a nitrogen atmosphere until a dark-brown solution is formed. The reaction mixture is then maintained under moderate reflux for 19 hours in an oil bath, with stirring. The mixture is then divided into 2 portions. To one portion there are added a further 1.12 g of 2-methoxyethoxymethyl-6-trifluoromethylnicotinic acid, 0.06 g of ZnCl$_2$ and 0.6 g of Hünig's base. The reaction mixture is then maintained under moderate reflux for 12 hours in an oil bath, with stirring. The solution is then washed twice with 0.1M hydrochloric acid (20 ml each time) and twice with water (20 ml each time). After drying the organic solution using magnesium sulfate and concentrating in vacuo, 3.9 g of 4-(2-methoxyethoxymethyl-6-trifluoromethyl-pyridin-3-ylcarbonyloxy)-bicyclo[3.2.1]oct-3-en-2-one are obtained in the form of a brown oil.

MS: 399 (M$^+$), 380, 354, 262, 230, 202, 187, 159, 139, 121, 91.

$^1$H NMR (CDCl$_3$): 1.65-1.75 (m, 2H), 2.05-2.30 (m, 4H), 3.00 (br t, 1H), 3.10 (br s, 1H), 3.35 (s, 3H, OC$\underline{H}_3$), 3.50 (m, 2H, CH$_2$C$\underline{H}_2$O), 3.70 (m, 2H, OC$\underline{H}_2$CH$_2$), 5.00 (s, 2H, ar. C$\underline{H}_2$), 5.90 (s, 1H, C═C$\underline{H}$), 7.75 (d, 1H. ar. $\underline{H}$), 8.30 (d, 1H. ar. $\underline{H}$).

EXAMPLE P11

Preparation of 4-hydroxy-3-(2-methoxyethoxymethyl-6-trifluoromethyl-pyridin-3-ylcarbonyl)-bicyclo[3.2.1]oct-3-en-2-one

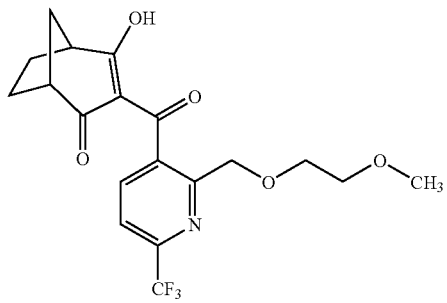

To a mixture of 200 mg (1.15 mmol) of 4-chlorobicyclo[3.2.1]oct-3-en-2-one (Preparation Example P2), 16 mg (0.12 mmol) of ZnCl$_2$, 324 mg (1.15 mmol) of 2-methoxyethoxymethyl-6-trifluoromethylnicotinic acid and 2 ml of toluene there are added dropwise, under a nitrogen atmosphere, over the course of 15 minutes, 166 mg (1.27 mmol) of diisopropylethylamine. A further 2 ml of toluene are then added and, with stirring, the reaction mixture is maintained under moderate reflux for 23 hours in an oil bath. The reaction mixture is then cooled to ambient temperature, and 4 ml of acetonitrile, 2 drops of cyanohydrin, 465 mg of triethylamine and a further 1 ml of acetonitrile are added. After drying the organic phase using magnesium sulfate and concentrating in vacuo, 452 mg of 4-hydroxy-3-(2-methoxyethoxymethyl-6-trifluoromethyl-pyridin-3-ylcarbonyl)-bicyclo[3.2.1]oct-3-en-2-one are obtained in the form of a viscous oil.

MS: 399 (M$^+$), 380, 356, 340, 310, 282, 256, 228, 202, 174, 152, 128, 67, 45.

$^1$H NMR (CDCl$_3$): 1.70-1.80 (m, 2H), 2.05-2.30 (m, 4H), 2.90 (br s, 1H), 3.15 (br s, 1H), 3.30 (s, 3H, OC$\underline{H}_3$), 3.40 (m, 2H, CH$_2$C$\underline{H}_2$O), 3.50 (m, 2H, OC$\underline{H}_2$), 4.75 (s, 2H, ar. C$\underline{H}_2$), 7.60 (s, 2H, ar. $\underline{H}$).

What is claimed is:

1. A process for the preparation of a compound of formula I

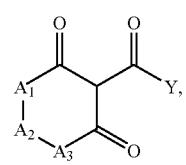

wherein Y is an organic substituent which is so selected that the compound of formula I has a pK value of from 1 to 5;

A$_1$ is CR$_1$R$_2$;

A$_2$ is oxygen, C(O), SO$_2$ or (CR$_3$R$_4$)$_n$;

n is 1 or 2;

A$_3$ is CR$_5$R$_6$;

R$_1$, R$_2$, R$_3$, R$_4$, R$_5$ and R$_6$ are each independently of the others C$_1$-C$_4$alkyl which may be mono-, di- or tri-substituted by C$_1$-C$_4$alkoxy, halogen, hydroxy, cyano, hydroxycarbonyl, C$_1$-C$_4$alkoxycarbonyl, C$_1$-C$_4$alkylthio, C$_1$-C$_4$alkylsulfinyl, C$_1$-C$_4$alkylsulfonyl, C$_1$-C$_4$alkylcarbonyl, phenyl or by heteroaryl, it being possible for the phenyl and heteroaryl groups in turn to be mono-, di- or tri-substituted by C$_1$-C$_4$alkoxy, halogen, hydroxy, cyano, hydroxycarbonyl, C$_1$-C$_4$alkoxycarbonyl, C$_1$-C$_4$alkylsulfonyl or by C$_1$-C$_4$haloalkyl, the substituents on the nitrogen in the heterocyclic ring being other than halogen;

and/or R$_1$, R$_2$, R$_3$, R$_4$, R$_5$ and R$_6$ are each independently of the others hydrogen, C$_1$-C$_4$alkoxy, halogen, hydroxy, cyano, hydroxycarbonyl, C$_1$-C$_4$alkoxycarbonyl, C$_1$-C$_4$alkylthio, C$_1$-C$_4$alkylsulfinyl, C$_1$-C$_4$alkylsulfonyl, C$_1$-C$_4$alkylcarbonyl, phenyl or heteroaryl, it being possible for the phenyl and heteroaryl groups in turn to be mono-, di- or tri-substituted by C$_1$-C$_4$alkoxy, halogen, hydroxy, cyano, hydroxycarbonyl, C$_1$-C$_4$alkoxycarbonyl, C$_1$-C$_4$alkylsulfonyl or by C$_1$-C$_4$haloalkyl, the substituents on the nitrogen in the heterocyclic ring being other than halogen; and/or R$_1$ and R$_2$ together form a 3- to 5-membered carbocyclic ring which may be substituted by C$_1$-C$_4$alkyl and/or interrupted by oxygen, sulfur, S(O), SO$_2$, OC(O), NR$_7$ or by C(O); and/or R$_2$ and R$_4$ together or R$_2$ and R$_5$ together form a C$_1$-C$_3$alkylene chain which may be interrupted by oxygen, sulfur, SO, SO$_2$, OC(O), NR$_8$ or by C(O); it being possible for that C$_1$-C$_3$alkylene chain in turn to be substituted by C$_1$-C$_4$alkyl; and R$_7$ and R$_8$ are each independently of the other C$_1$-C$_4$alkyl, C$_1$-C$_4$haloalkyl, C$_1$-C$_4$alkylsulfonyl, C$_1$-C$_4$alkylcarbonyl or C$_1$-C$_4$alkoxycarbonyl; in which process a) a compound of formula II

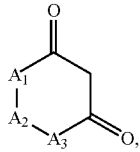

(II)

wherein $A_1$, $A_2$ and $A_3$ are as defined for formula I, is reacted, in the presence of a water-immiscible solvent, in the presence of a base or a catalytic amount of a tertiary amide, either with a chlorination or bromination agent or with a compound of formula III Cl—SO$_2$R$_9$     (III), wherein $R_9$ is $C_1$-$C_4$alkyl, $C_1$-$C_4$haloalkyl, phenyl or $C_1$-$C_4$alkyl-substituted phenyl, to form the compound of formula IV

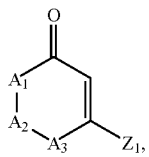

(IV)

wherein $A_1$, $A_2$ and $A_3$ are as defined for formula I and Z1 is chlorine, bromine or OSO$_2$R$_9$, $R_9$ being as defined hereinbefore;

b) the compound of formula IV is converted, using a compound of formula V

M$^+$-O$^-$—C(O)—Y     (V), wherein Y is as defined hereinbefore and M$^+$ is the hydrogen cation or an alkali metal ion, alkaline earth metal ion or ammonium ion, into the compound of formula VI

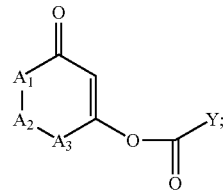

(VI)

and c) then the compound of formula VI is treated with a cyanide source in the presence of a base.

2. Compounds of formulae IVa and IVb

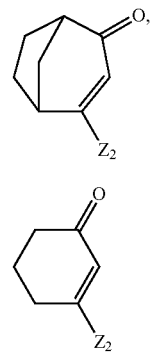

(IVa)

(IVb)

wherein $Z_2$ is chlorine, bromine or OSO$_2$R$_9$, and $R_9$ is $C_1$-$C_4$alkyl, $C_1$-$C_4$haloalkyl, phenyl or $C_1$-$C_4$alkyl-substituted phenyl; wherein, if the compound has the formula IVb, then $Z_2$ is not chlorine or bromine and $R_9$ is not methyl, tolyl or CF$_3$.

3. The compound according to claim 2, wherein the compound is of formula IVa and $Z_2$ is selected from the group consisting of chorine, bromine and —OSO$_2$CH$_3$.

* * * * *